United States Patent [19]

Gordon, III

[11] Patent Number: 5,064,411
[45] Date of Patent: Nov. 12, 1991

[54] PROTECTIVE MEDICAL DEVICE

[76] Inventor: Kilbourn Gordon, III, 178 N. Deerwood, Orange, Calif. 92669

[21] Appl. No.: 542,189

[22] Filed: Jun. 22, 1990

Related U.S. Application Data

[62] Division of Ser. No. 267,029, Nov. 4, 1988, abandoned.

[51] Int. Cl.⁵ .................... A61B 10/00; A61B 17/00; A61M 5/00; F41H 1/02
[52] U.S. Cl. .................................. 604/48; 128/763; 128/753; 128/754; 128/846; 604/51; 604/239; 604/272; 604/274; 606/167; 606/222; 2/2.5; 2/DIG. 7
[58] Field of Search ............... 604/48, 51, 272, 273, 604/274, 55, 239, 53, 54; 128/763, 846, 749, 753, 754; 2/2.5, 161 R, DIG. 7; 606/222, 167

[56] References Cited

U.S. PATENT DOCUMENTS

| 2,748,769 | 6/1956 | Huber . | |
|---|---|---|---|
| 3,175,544 | 3/1965 | Stewart . | |
| 3,916,448 | 11/1975 | Hamel | 2/161 R |
| 4,004,295 | 1/1977 | Byrnes, Sr. . | |
| 4,205,689 | 6/1980 | Brennan | 128/743 |
| 4,222,392 | 9/1980 | Brennan | 128/743 |
| 4,384,449 | 5/1983 | Byrnes, Sr. | 57/210 |
| 4,388,733 | 6/1983 | Anstett . | |
| 4,433,439 | 2/1984 | Sidman et al. | 2/161 R |
| 4,470,251 | 9/1984 | Bettcher . | |
| 4,490,139 | 12/1984 | Huizenga et al. | 604/57 |
| 4,493,865 | 1/1985 | Kuhlmann et al. . | |
| 4,526,828 | 7/1985 | Fogt et al. . | |
| 4,578,826 | 4/1986 | Adiletta . | |
| 4,742,578 | 5/1988 | Seid | 2/2.5 |

FOREIGN PATENT DOCUMENTS

| 0446818 | 7/1927 | Fed. Rep. of Germany | 604/272 |
|---|---|---|---|
| 1457657 | 11/1966 | France | 604/272 |
| 956082 | 4/1964 | United Kingdom . | |

Primary Examiner—Robert A. Hafer
Assistant Examiner—Brian E. Hanlon
Attorney, Agent, or Firm—Knobbe Martens Olson & Bear

[57] ABSTRACT

An apparatus and method for protecting users of invasive instruments from inadvertent skin puncture by providing the user with an article of protective clothing and an invasive instrument both designed so that the instrument will become entangled with the clothing during contact, thereby preventing penetration of the skin.

43 Claims, 2 Drawing Sheets

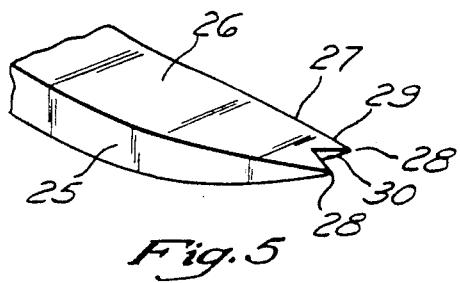
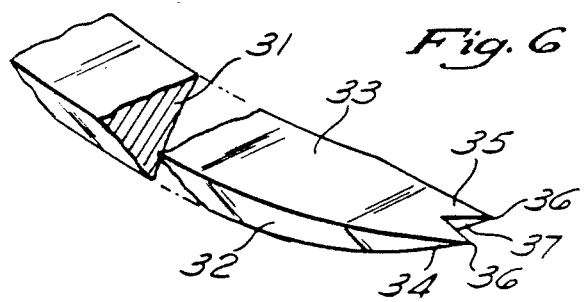
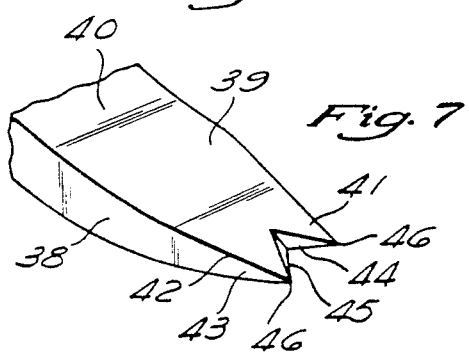
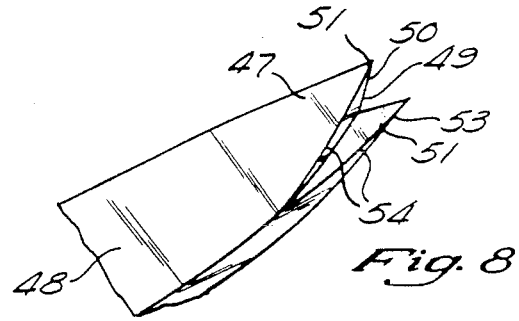
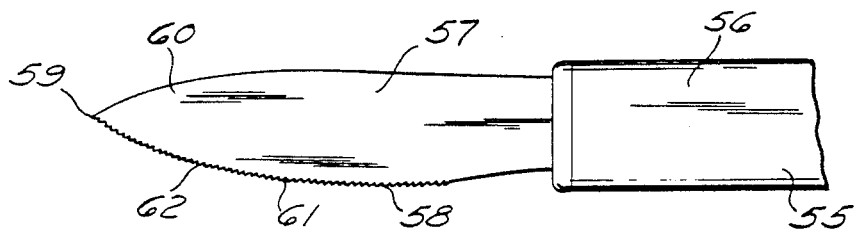
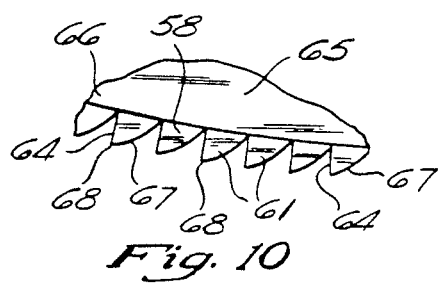
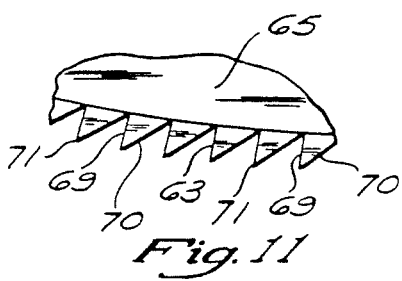

PROTECTIVE MEDICAL DEVICE

This application is a division of application Ser. No. 07/267,029, filed Nov. 4, 1988, abandoned.

BACKGROUND OF THE INVENTION

The present invention relates generally to an apparatus and method of protecting users of invasive instruments from inadvertent puncture of their skin. More specifically, the present invention relates to an apparatus and method for protecting users of invasive medical instruments such as scalpels or needles from being exposed to infection or disease via inadvertent needle sticks or other skin puncture.

Users of invasive instruments such as knives, needles or scalpels are constantly exposed to the dangers of puncturing or cutting their skin, specifically their hands, when working with such instruments. Such punctures can be of particular concern if the instrument has previously been exposed to a patient carrying any of a variety of dangerous chemical and biologic substances, such as HIV or Hepatitis B virus.

The prior art in the area has focused on the protection of the hands and arms with reinforced gloves and gauntlets which are impervious to the specific instrument used; for instance, protective butchers' gloves in association with butchers' knives or cleavers. See e.g., U.S. Pat. Nos. 3,916,448, 4,004,295 and 4,388,733. In addition, the prior art emphasizes protection only via the covering of the skin with an impervious covering, not via a method wherein the skin covering is specifically associated with a modified instrument as to prevent skin puncture.

The aforementioned protective methods have not addressed the problem wherein users work with very fine and delicate instruments, or require a full range of motion or sensitivity in the hands. For these users, a large, impervious glove, such as those used by butchers, would not be satisfactory.

In addition, persons working in the scientific or health care professions handle invasive instruments which are exposed to a variety of dangerous chemical and biologic substances, such as the HIV or Hepatitis B virus. Since such scientific and health care workers generally use very fine and delicate instruments, require an extended range of motion or sensitivity, or both in the hands, and are exposed to dangerous substances which can be transmitted to the worker by an extremely small wound to the skin, an effective method for protecting these users from inadvertent puncture by these invasive instruments is needed.

SUMMARY OF THE INVENTION

An object of this invention is to prevent cutting or puncturing of the skin during the use of sharpened invasive instruments by providing the user with an article of protective clothing made of fibrous material and with an invasive instrument wherein the instrument has more than one adjacent point at the sharpened portion. During contact between the invasive instrument and the fibrous material of the clothing, the points of the instrument and the fibers of the material are adapted to be entangled in such a way as to prevent penetration of the points through the clothing, in turn preventing penetration of the points into the skin of the user.

The invasive instrument may comprise a variety of surgical instruments, specifically, it may comprise any type of needle; for instance, a pointed cannula or a type of hypodermic, surgical or suturing needle. In addition, the invasive instrument may comprise a type of cutting or slicing blade; for instance a cutting or surgical scalpel.

The article of protective clothing may advantageously comprise a woven or knitted material, which is preferably comprised of a plurality of layers. Most preferably the clothing will take the form of a glove.

The scalpel and needles used in this method, will have serrations producing at least two adjacent points at the tip, in the case of a needle, or, a plurality of serrations along the blade, in the case of a scalpel. In the event a plurality of serrations are produced on the instrument, they will be separated by a distance preferably no greater than about 3 mm, and most preferably, no greater than about 2 mm or 1 mm. In addition, the depth of each individual serration between the points would preferably be no greater than about 3 mm, and most preferably, no greater than about 2 mm or 1 mm.

Another object of this invention is to provide a system to prevent skin penetrating injury to a user of sharpened, invasive instruments, which comprises, in combination, an article of protective fibrous clothing and a sharpened invasive instrument having at least two adjacent points at its sharpened portion which are adapted to entangle the fibers of the fibrous clothing on contact, thereby preventing penetration of the points of the instrument through the clothing and into the skin of the user.

The article of protective fibrous clothing is preferably woven or knitted, has a plurality of layers, and most preferably is in the form of a glove.

It is preferred that the depth of the individual serrations are not substantially greater than the thickness of the clothing involved, so that the points, when entangled in the fibrous material of the clothing, cannot penetrate the skin. In any event, the depth of the serrations are preferably no greater than about 3 mm and most preferably no greater than about 2 mm, or even 1 mm.

The invasive instruments may comprise any of a variety of surgical instruments. For instance, it may comprise any type of needle, such as a pointed cannula or a hypodermic, surgical or suturing needle. In addition, the invasive instrument may comprise a cutting or slicing blade; for instance, a cutting or surgical scalpel.

DESCRIPTION OF THE DRAWINGS

FIG. 5 is an enlarged perspective view of the tip of the suturing needle in FIG. 4, depicting a rhomboidal shaft with a tapered, sharpened point comprising a serrated tip.

FIG. 6 is an enlarged perspective view of the tip of the suturing needle in FIG. 4, depicting a triangular shaft with a sharpened point comprising a serrated tip.

FIG. 7 is an enlarged top perspective view of the serrated tip of the suturing needle in FIG. 5.

FIG. 8 is an enlarged bottom perspective view of the serrated tip of the suturing needle in FIG. 6.

FIG. 9 is an enlarged side view of a surgical scalpel, depicting the blade end with its associated serrated cutting edge.

FIG. 10 is an enlarged side view of the surgical scalpel of FIG. 9, depicting the blade end and the orientation of the serrated cutting edge, with each individual serration comprising a leading edge perpendicular to the cutting edge and a curved trailing edge, both edges combining to form a sharpened point.

FIG. 11 is an enlarged side view of the surgical scalpel of FIG. 9, depicting the blade end and the orientation of the serrated cutting edge, with each individual serration comprising a leading edge perpendicular to the cutting edge, and a straight trailing edge, both edges combining to form a sharpened point.

DESCRIPTION OF THE PREFERRED EMBODIMENT

A variety of articles of protective clothing in which this invention may be applied include gloves, gauntlets, wrist guards, finger covers, aprons, shirts and trousers. A preferred embodiment of the protective clothing may be in the form of a glove. In addition, the fibrous material may be supplied as individual patches or pieces applicable directly to the skin, preferably in the form of a bandage to cover critically exposed areas of the skin.

Figure 1:
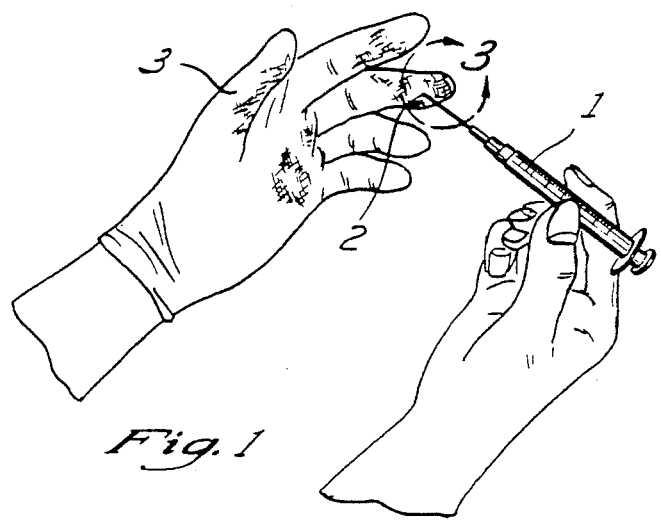
FIG. 1 is a representation of an application of the protective medical device, consisting of a hypodermic needle and protective glove in combination, depicting the serrated needle tip in association with the protective glove; specifically, with a number of woven fibers lying between the points of the needle.
Figure 2:
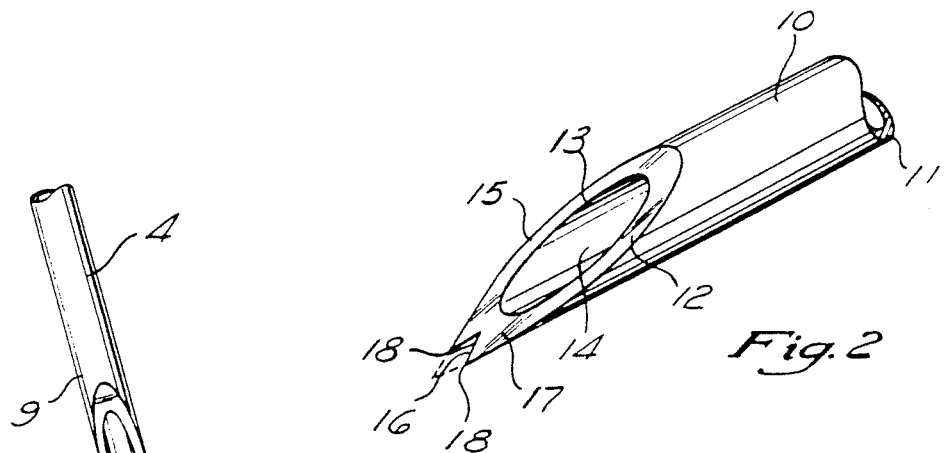
FIG. 2 is an enlarged perspective view of the outlet of the needle, displaying the beveled, serrated tip, having two points.
Figure 3:
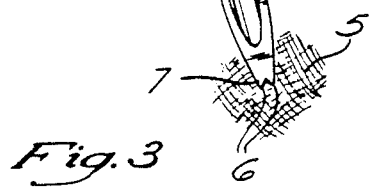
FIG. 3 is an enlarged side view of the needle in conjunction with the woven fibers contained in the associated glove as viewed in FIG. 1.

Referring now to FIGS. 1, 2 and 3, there is depicted a specific embodiment of the invention, namely a hypodermic needle 1 having a serrated point 2 and its associated glove 3 comprised of the appropriate fibrous material as in FIG. 1.

The glove is comprised of a composition of fibers, such as, but not limited to, metal wire, an aramid fiber such as Kevlar, a polyester fiber, a polyamide fiber, other synthetic fibers, naturally occurring fibers, elastic fibers or a combination of them.

Preferably, the glove is comprised of double-knit polyester fiber, woven polyester, woven nylon, or woven cotton fibers. The fibers must be flexible enough to be formed into a glove for the hand and the fabric may be made by methods which include, but are not limited to, weaving, knitting, sewing or layering the fibers together to form the appropriate fiber matrix. Preferably, the fibers may comprise more than one layer, and most preferably, at least two layers, with the weave of the layers preferably oriented at angles to each other, such as about 45°.

The fiber matrix glove or other article of protective clothing may be used with a group or grouping of specific invasive instruments. The optimum construction of the glove and its fiber matrix is determined by a number of factors and measures. These factors and measures may include, but are not limited to, the composition, tensile strength and number of layers of the fiber composition, along with the number and configuration of the serrations in their invasive instrument. In any case, the diameter of the points of the invasive instrument should not exceed the thickness of the matrix.

The construction of the glove may further be altered in accordance with the number, spacing, size, cut, use and configuration of the invasive instrument and its serrations and their associated points.

The depth of the serration between the points should not be greater than about the thickness of the fabric of the protective clothing, which may be up to 3 mm thick, but is usually less than 2 mm and often less than 1 mm thick.

A preferred embodiment of the invention may comprise a thin, finely woven material such as nylon as the fibrous material. Preferably, the woven material will comprise a plurality of layers in conjunction with a correspondingly shallow depth of the serrations found in the invasive instrument, calculated as to prevent skin puncture during their association.

Another preferred embodiment of the invention may comprise a finely knitted material, such as double-knit polyester, as the fibrous material. Preferably, a plurality of layers of the knitted material will be used, and most preferably, one layer. Again, the knitted material in this preferred embodiment is comprised of a thickness in conjunction with a correspondingly shallow depth of serrations of the invasive instrument, calculated as to prevent skin puncture during their association.

These combinations are preferred embodiments as they may provide maximum dexterity to the wearer due to the fine weave of the material, and maximum protection of the skin due to the thickness of the fibrous material in relation to the shallow depth of the serrations.

In a contemplated use of the invention, the invasive instrument in combination with its associated glove will prevent inadvertent hand skin contact with the invasive instrument as depicted in FIG. 1.

FIG. 3 depicts a contemplated mode of association between the fibrous material 5 and the serrations 7 of the invasive instrument 9, in this depiction a hypodermic needle 4, wherein the invasive instrument 9 has an appropriate number and configuration of serrations 7 to (1) allow it to be used in its contemplated mode as an invasive instrument; and (2) to allow the serrations 7 to become sufficiently intertwined with the fibrous material 5 as to prevent the points 6 of the invasive instrument 7 from coming into contact with the skin of the user.

Most preferably, a plurality of individual fibers 8 will be caught between the individual points 6 of the needle 4, thereby producing a cumulative fibrous thickness exceeding that of the depth of the serrations 7, thereby preventing skin contact by the points 6 of the invasive instrument 9.

The sharpened points 6 associated with the serrations 7 allow the invasive instrument 9 to pierce or cut the skin in a manner producing discomfort and damage not substantially different in kind or duration from that produced by corresponding conventional instruments.

When entangled with the fibrous material 5, it has been determined that such sharpened points 6 do not substantially cut the individual fibers 8 that become entangled in said serrations 7.

Referring to FIG. 2, there is depicted a specific embodiment of one invasive instrument of the present invention. FIG. 2 shows a hypodermic needle 10 comprised of a hollow wall 11 defining a lumen 12 with an opening 13 at the end of a cannula 14, terminating with a beveled end surface 15 at a 25° angle to the axial line of cannula 14. The distal end of the beveled surface 15 has a serration 16 cut into the tip 17 of the needle 10. FIG. 2 depicts a hypodermic needle tip 17 with one serration 16 incorporated into the tip 17 of the needle 10, thereby terminating the needle 10 in two points 18. It will be understood, however, that more than two points could be used.

Referring to FIGS. 4-7, there is depicted another embodiment of the invention in the form of a surgical needle and its associated suture material.

Figure 4:
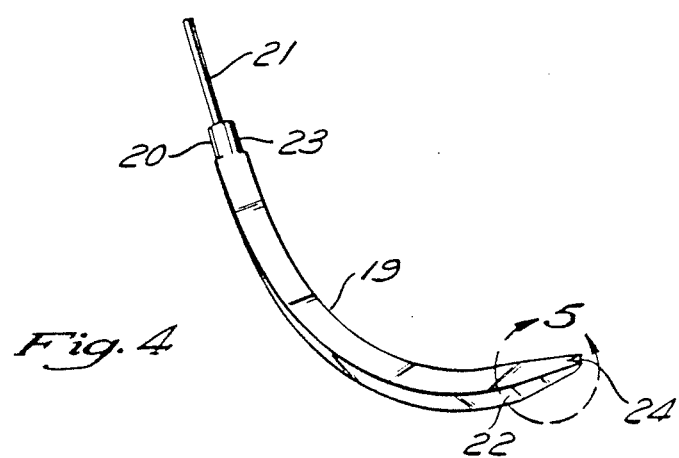
FIG. 4 is an enlarged perspective view of a suturing needle, with the serrated tip indicated.

Referring the FIG. 4, the needle 19 comprises a distal end 20 and its associated suture material 21, and a proximal end 22 which comprises a semi-circular shaft 23 ending in a serrated needle tip 24. The needle 19 may advantageously be formed from a solid material in a generally rectangular, rhomboidal triangular or square cross-sectional form, gradually tapered into a curved, pointed proximal end 22 with the serrated tip 24.

Referring to FIG. 5, an embodiment of a suturing needle tip is depicted, corresponding to a cross-sectionally rhomboidal needle of FIG. 4, wherein the sides 25 and top 26 of the needle 27 are gradually tapered and curved, terminating in sharpened points 28. The tip 29 has one serration 30 cut into it, thereby terminating the needle 27 in two sharpened points 28.

Referring to FIG. 6, another embodiment of a suturing needle tip is depicted, corresponding to a cross-sectionally triangular needle 31 of FIG. 4, wherein the sides 32 and top 33 of the needle 31 are gradually tapered and curved, and the sides 32 of the needle 31 gradually taper into the proximal tip 34 which curves into the leading top edge 35 of the needle 31, terminating in sharpened points 36. The tip 34 has one serration 37 cut into it, thereby terminating the needle 31 into two points 36.

Referring to FIG. 7, an enlarged view of the proximal end of the suturing needle in FIG. 5 is depicted, wherein the sides 38 and top 39 of the needle 40 gradually curve to a point 41, providing a flattened, sharpened edge 42 at the proximal end 43 of the needle 40. The proximal end 43 of the needle 40 in FIG. 7 consists of a single serration 44 cut into the point 41 of the needle 40, with such cut performed at an angle to the leading edge as to provide for a sharpened inner edge 45. The points 46 at the proximal end 43 of the needle 40 may be formed by the same process cut as the serration 44, thereby terminating the needle 40 into two sharpened points 46 at about 45° angles to the horizontal sides 38 of the proximal end 44 of the needle 30.

Referring to FIG. 8, the enlarged bottom perspective view of the proximal tip 34 of the cross-sectionally triangular suturing needle 31 in FIG. 6 is depicted. The proximal end 47 of the needle 48 in FIG. 8 consists of a single serration 49 cut into the proximal end 47 of the needle 48, with such cut performed at an angle as to provide for a sharpened inner edge 50. Each of the needle points 51 are triangular in cross-section and the edges 42 where the two surfaces of the triangles meet comprise a gradually proximally tapered, sharpened edge 53 and two sharpened bottom edges 54.

In a contemplated mode of use of the invention, the suturing needles as depicted in FIGS. 4-8 in combination with the associated glove or other protective clothing will prevent inadvertent contact between the user's skin and the suturing needles.

Preferably, in the event of inadvertent contact of the gloved hand with the tip of the suturing needle, a plurality of individual fibers which comprise the glove will be caught between the individual points of the needle within the serration, producing a cumulative fibrous thickness exceeding that of the depth of the serrations, thereby preventing skin contact by the points of the invasive instrument.

FIG. 9 depicts a surgical scalpel 55 consisting of a handle 56 attached to a blade 57 which is sharpened to an edge 58 and comes to a point 59 on the proximal end 60 of the scalpel 55. The cutting edge 58 of the scalpel 55 has a number of serrations 61 cut into it, ranging along the entire cutting edge 58 of the blade 57. Each individual serration 61 in this embodiment of the invention is cut on a radius 62, and terminates in the same fashion.

FIGS. 10 and 11 depict the cutting edge 58 of the scalpel 55 of FIG. 9, specifically the serrations 61 cut into the edge 58. The serrations 61 incorporated into the scalpel 55 may be varied as to number, shape, depth and cut angle and may be cut into the edge of the instrument in a variety of methods, such as via laser, die stamp, machine lock or cutting wire.

FIG. 10 shows individual serrations 63 with each individual serration 63 comprising a leading edge 64 perpendicular to the body of the scalpel 65, facing the proximal end 66 of the scalpel 65 and a curved trailing edge 67, with both edges 64, 67 terminating at a point 68.

FIG. 11 shows another possible configuration of the serrations 63, wherein the leading edge 69 is again perpendicular to the body of the scalpel 65, and the trailing edge 70 is straight and at about 60° to the body of the scalpel 65, with both edges 69, 70 terminating at a point 71.

In a contemplated mode of use of the invention, the scalpels as depicted in FIGS. 9-11, in combination with their associated glove will prevent inadvertent hand skin contact by the scalpels. Most preferably, in the event of inadvertent contact of the gloved hand by the cutting edge of the scalpel blade; or, by the edge of the scalpel blade as the blade travels in a forward motion tip first across the glove; a plurality of individual fibers which comprise the glove will be caught between the individual points of the needle within the serrations, producing a cumulative fibrous thickness exceeding that of the depth of the serrations, thereby preventing skin contact by the cutting edge or the tip of the scalpel.

It has been determined that the sharpened points and edges of the scalpel blade in which the serrations are cut allow for the normal use of the blade as a cutting instrument. In addition, when entangled with the fibrous material, it has been determined that the sharpened points and edges of the individual serrations do not substantially cut the individual fibers which become entangled in said serration.

I claim:

1. A method for preventing cutting or puncturing of the skin during use of a sharpened invasive medical instrument, comprising the steps of:
   providing a user with a sharpened invasive medical instrument,
   providing said user with an article of protective clothing made of fibrous material, wherein said instrument has more than one adjacent point at the sharpened portion thereof and wherein said points are in a fixed relationship to each other, which points are exposed to the user during the use and which are separated by a valley; and
   entangling the points of said invasive instrument in said fibrous material upon contact between said instrument and said clothing, wherein the distance between said points and the depth of said valley are sufficiently small that during engagement of said instrument and said clothing, said points and the fibers of said material entangle and the depth of entangled fibers within said valley is equal to or greater than the depth of said valley such that, thereby preventing penetration of said points through said clothing into the skin of the user.

2. The method of claim 1, wherein said instrument is a scalpel.

3. The method of claim 2, wherein said scalpel has a serrated cutting edge.

4. The method of claim 3, wherein said serrated cutting edge consists of a plurality of serrations.

5. The method of claim 4, wherein said serrations are individually separated by a distance no greater than about 3 mm.

6. The method of claim 5, wherein said distance is no greater than about 1 millimeter.

7. The method of claim 4, wherein said plurality of serrations causes said scalpel to have a plurality of adjacent points along the cutting edge, wherein the depth of the serration between said prongs is no greater than about 3 mm.

8. The method of claim 7, wherein said depth is no greater than about 2 mm.

9. The method of claim 1, wherein said instrument is a suture needle.

10. The method of claim 1, wherein said instrument is a needle.

11. The method of claim 10, wherein said needle has a serrated tip.

12. The method of claim 11, wherein said serration causes said needle to have at least two adjacent prongs at said tip, wherein the depth of the serration between said prongs is no greater than about 3 mm.

13. The method of claim 12, wherein said depth is no greater than about 2 mm.

14. The method of claim 13, wherein said needle is a hypodermic needle.

15. The method of claim 1, wherein said clothing is a glove.

16. The method of claim 1, wherein said clothing comprises multiple layers.

17. The method of claim 1, wherein said clothing is knitted.

18. The method of claim 1, wherein said clothing is woven.

19. A system for preventing skin-penetrating injury to a user of a sharpened invasive medical instrument, comprising in combination:
an article of protective fibrous clothing; and
a sharpened invasive medical instrument having at least two adjacent points in fixed relation to each other at the sharpened portion thereof, wherein said points are exposed to the user during use, and are separated from each other by a valley, wherein the distance between said points and the depth of said valley are sufficiently small that during engagement of said instrument and said clothing, said points entangle in the fibers of said clothing, and the depth of entangled fibers within the valley is equal to or greater than the depth of said valley, thereby preventing penetration of said instrument through said clothing into the skin of the user.

20. The system of claim 19, wherein said instrument is a scalpel.

21. The system of claim 20, wherein said scalpel has a serrated cutting edge.

22. The system of claim 21, wherein said serrated cutting edge consists of a plurality of serrations.

23. The system of claim 22, wherein said serrations are individually separated by distance no greater than about 3 mm.

24. The system of claim 23, wherein said distance is no greater than about 1 millimeter.

25. The system of claim 22, wherein said plurality of serrations causes said scalpel to have a plurality of adjacent points along the cutting edge, wherein the depth of the serration between said points is no greater than about 3 mm.

26. The system of claim 25, wherein said depth is no greater than about 2 mm.

27. The system of claim 19, wherein said needle is a suture needle.

28. The system of claim 19, wherein said needle is a hypodermic needle.

29. The system of claim 19, wherein the depth of said serration is not substantially greater than the thickness of said clothing, so that said points, when entangled in said fibrous material, do not penetrate the skin.

30. The system of claim 27, wherein said depty is no greater than about 2 mm.

31. The system of claim 19, wherein the depth of said serration is no greater than about 3 mm.

32. The system of claim 19, wherein said instrument is a needle.

33. The system of claim 32, wherein said needle has a serrated tip.

34. The system of claim 33, wherein said serration causes said needle to have at least two adjacent points at said tip, wherein the depth of the serration between said points is no greater than about 3 mm.

35. The system of claim 34, wherein said depth is no greater than about 2 mm.

36. The system of claim 19, wherein said clothing is a glove.

37. The system of claim 19, wherein said clothing comprises multiple layers.

38. The system of claim 19, wherein said clothing is knitted.

39. The system of claim 19, wherein said clothing is woven.

40. A needle for invasive medical use having a sharpened distal end and a plurality of points at said distal end such that the points forming the invasive end of said needle are at a fixed distance in relation to each other and the space between each adjacent point forms a valley having a depth no greater than about 1 mm.

41. The needle of claim 40, in the form of a hypodermic needle.

42. The needle of claim 40, in the form of a suture needle.

43. The needle of claim 40, wherein said points are adapted to penetrate nonfibrous material, but are adapted to become entangled in fibrous material.

* * * * *